(12) United States Patent
Shan et al.

(10) Patent No.: US 12,005,430 B2
(45) Date of Patent: Jun. 11, 2024

(54) CATALYST SYSTEM AND LIGHT HYDROCARBON AROMATIZATION METHOD, CARBON DIOXIDE HYDROGENATION PROCESS AND METHOD FOR ENHANCING CATALYST LIFETIME

(71) Applicants: China Energy Investment Corporation Limited, Beijing (CN); National Institute of Clean-and-Low-Carbon Energy, Beijing (CN)

(72) Inventors: Junjun Shan, San Jose, CA (US); Louis Guillen, San Jose, CA (US); Hui Wang, Fremont, CA (US); Aihua Zhang, San Bruno, CA (US); Lisa Nguyen, Santa Clara, CA (US); Joshua Miles, San Francisco, CA (US); Saydul Sardar, Santa Clara, CA (US); Hua Liu, Beijing (CN)

(73) Assignees: China Energy Investment Corporation Limited, Beijing (CN); National Institute of Clean-And-Low-Carbon Energy, Beijing (CN)

( * ) Notice: Subject to any disclaimer, the term of this patent is extended or adjusted under 35 U.S.C. 154(b) by 8 days.

(21) Appl. No.: 17/703,437

(22) Filed: Mar. 24, 2022

(65) Prior Publication Data
US 2023/0249163 A1    Aug. 10, 2023

(30) Foreign Application Priority Data
Feb. 9, 2022 (CN) .......... 202210121303.3

(51) Int. Cl.
*B01J 29/06* (2006.01)
*B01J 29/70* (2006.01)
*B01J 37/02* (2006.01)
*C01B 32/40* (2017.01)
*C07C 2/76* (2006.01)

(52) U.S. Cl.
CPC ....... *B01J 29/7049* (2013.01); *B01J 37/0201* (2013.01); *C01B 32/40* (2017.08); *C07C 2/76* (2013.01); *C07C 2529/70* (2013.01)

(58) Field of Classification Search
CPC ......... C07C 2/76; C07C 2/82; C07C 2529/70; C07C 2529/54; C07C 15/08; C07C 15/06; C07C 15/04; C10G 50/00; C10G 2300/1081; C10G 2400/30; C01B 32/40; B01J 38/12; B01J 35/00; B01J 35/0006; B01J 35/18; B01J 37/0009; B01J 37/088; B01J 37/0201; B01J 37/0215; B01J 37/18; B01J 2229/20; B01J 2229/186; B01J 29/90; B01J 29/7049; B01J 29/06; B01J 29/061; B01J 29/064; B01J 29/068; B01J 29/072; B01J 29/405; B01J 29/44; B01J 29/46; B01J 29/48; B01J 29/74; B01J 29/76; B01J 29/78; Y02P 20/52
USPC ............... 502/60, 61, 63, 64, 66, 69, 71, 74, 502/527.12, 527.13
See application file for complete search history.

(56) References Cited

U.S. PATENT DOCUMENTS

| | | | |
|---|---|---|---|
| 4,157,293 A | 6/1979 | Plank et al. | |
| 4,849,568 A | 7/1989 | McCullen et al. | |
| 6,534,431 B1 | 3/2003 | Suntola et al. | |
| 8,652,429 B2* | 2/2014 | Sumiya | B01J 37/0244 60/299 |
| 8,809,608 B2 | 8/2014 | Lauritzen et al. | |
| 8,946,107 B2 | 2/2015 | Lauritzen et al. | |
| 8,969,228 B2* | 3/2015 | Nazarpoor | B01J 23/10 502/514 |
| 9,034,269 B2* | 5/2015 | Hilgendorff | B01J 37/0246 502/262 |
| 2017/0087541 A1* | 3/2017 | Andersen | B01J 35/0006 |
| 2019/0126247 A1* | 5/2019 | Deeba | B01J 37/0236 |

* cited by examiner

*Primary Examiner* — Elizabeth D Wood
(74) *Attorney, Agent, or Firm* — Calfee, Halter & Griswold LLP

(57) ABSTRACT

The present disclosure relates to the catalytic field, and discloses a catalyst system and a light hydrocarbon aromatization method, a carbon dioxide hydrogenation process and a method for enhancing the catalytic activity and/or lifetime of the catalyst during a heterogeneous catalysis process, the catalyst system comprising a porous material layer containing an active metal component and a molecular sieve layer. The catalyst system provided by the present disclosure exhibits desirable catalytic activity, stability, renewability and selectivity, thus has significant benefits.

17 Claims, 11 Drawing Sheets

CATALYST SYSTEM AND LIGHT HYDROCARBON AROMATIZATION METHOD, CARBON DIOXIDE HYDROGENATION PROCESS AND METHOD FOR ENHANCING CATALYST LIFETIME

CROSS REFERENCE TO RELATED APPLICATION

This application claims priority to CN 202210121303.3, which was filed Feb. 9, 2022 and is incorporated herein by reference as if fully set forth.

FIELD

The present disclosure relates to a catalyst system and a light hydrocarbon aromatization method, a carbon dioxide hydrogenation process and a method for enhancing the catalytic activity and/or lifetime of the catalyst during heterogeneous catalysis process.

BACKGROUND

Direct conversion of light alkanes to aromatic compounds is particularly interesting due to the importance of the aromatic compounds in the chemical industry. The metal-modified zeolite catalysts have been extensively studied in the aromatization of light alkanes so far.

For example, both U.S. Pat. Nos. 8,946,107B2 and 8,809,608B2 disclose a process for the selective conversion of ethane to aromatic hydrocarbons based on a Pt/ZSM-5 catalyst. In order to obtain a high selectivity of aromatic hydrocarbons, a second metal component is added to attenuate dehydrogenation of Pt.

Wherein U.S. Pat. No. 8,946,107B2 discloses a process for catalyzing ethane aromatization reaction by using Pt/ZSM-5, and further discloses adding a second metal Fe based on a loading amount of 0.005-0.15 wt % Pt to attenuate Pt, thereby reducing methane production and increasing BTX selectivity. Based on the disclosed catalytic performance, the addition of Fe surely increases BTX selectivity. However, when Fe is added as the second metal, the ethane conversion (i.e., catalytic activity of Pt) also decreases.

U.S. Pat. No. 8,809,608 describes a process of using Sn as the second metal to attenuate Pt in order to increase BTX selectivity. Adding Sn in various amounts appears to significantly reduce methane productivity and increase BTX selectivity compared to the Pt/ZSM-5 catalysts. However, similar to Fe, the presence of Sn also reduces the catalytic activity, as the conversion rate of ethane is also significantly reduced.

Another problem of the Pt-based catalysts is stability and lifetime of said catalysts. Due to the formation of coke, Pt-based catalysts deactivate very quickly and require continuous regeneration to maintain their activity. However, as described in literature, the regeneration cycles lower the catalyst activity of said Pt-based catalysts in the aromatization reaction. U.S. Pat. Nos. 8,946,107B2 and 8,809,608B2 also fail to address the problem of rapid deactivation and reduced catalytic activity of Pt-based catalysts after regeneration cycles.

U.S. Pat. No. 6,534,431B1 discloses a process and apparatus for preparing heterogeneous catalysts by evaporation of a catalyst reagent containing the catalytically active component or its precursor. The vapor is routed into a reaction chamber where it is brought to interact with the carrier material. A portion of the catalyst reagent can be bound to a surface of the carrier material. The catalyst reagent, which is not bound to the carrier, is purged from the reaction chamber in gaseous form. The component bound to the carrier is post-treated in order to convert it into a catalytically active form. The Zn-containing zeolites prepared with said method are found to have similar or even higher activity than the catalysts produced with the conventional wet impregnation methods. Although the Zn-based catalysts prepared with the method disclosed in U.S. Pat. No. 6,534,431B1 may have higher activity than the catalysts produced with the wet impregnation methods, the complex equipment obtained through the special design is required to prepare such catalysts. Furthermore, complex post-treatments are often required to activate the catalyst.

Both U.S. Pat. Nos. 4,157,293A and 4,849,568A describe a process for the conversion of light hydrocarbons to aromatic hydrocarbons based on the zinc-containing zeolites. However, as reported in U.S. Pat. No. 4,157,293A, because of Zn tends to elute from the zeolite carrier at high temperatures in a reducing atmosphere, it causes the reduced catalyst activity and stability. In order to address this problem, U.S. Pat. No. 4,157,293A discloses an aromatization process of stabilizing the Zn component by adding a second metal such as copper, nickel, germanium and rhenium to stop or significantly delay the elution of Zn, thereby allowing the catalyst to maintain a high activity level. For the sake of solving the Zn loss problem, U.S. Pat. No. 4,849,568A discloses a solution of adding at least one non-metal oxides (e.g., $H_2O$ or sulfide) to the feed materials during the aromatization reaction process. It is observed that the addition of a non-metal oxide or sulfide to the feed materials prevents the elution of Zn from the zeolite.

Although both U.S. Pat. Nos. 4,157,293A and 4,849,568A describe some methods of retarding Zn loss, both have limitations and disadvantages. In U.S. Pat. No. 4,157,293A, the addition of a second metal also decreases the catalyst activity and BTX selectivity. The addition of Cu and Ni also produces more coke, which causes more difficulty in the regeneration process. In the case of U.S. Pat. No. 4,849,568A, the addition of a non-metal oxide or sulfide to the feed materials indeed significantly dilute the concentration of light alkanes in the feed materials, thus reducing BTX productivity. The use of some non-metal oxides (e.g., $H_2O$) also results in dealumination of the zeolite, which decreases reactivity of the catalyst.

SUMMARY

An object of the present disclosure is to overcome the problems in the prior art, to further improve the catalyst activity and to increase the catalyst lifetime during the reaction process. The disclosure also provides a catalyst system and a light hydrocarbon aromatization method, a carbon dioxide hydrogenation process and a method for enhancing the catalytic activity and/or lifetime of the catalyst during a heterogeneous catalysis process.

In order to achieve the above object, a first aspect of the present disclosure provides a catalyst system comprising a porous material layer containing an active metal component and a molecular sieve layer.

In a second aspect, the present disclosure provides a light hydrocarbon aromatization method, the method comprises sequentially contacting the light hydrocarbons with the porous material layer and the molecular sieve layer of the catalyst system under light hydrocarbon aromatization conditions.

In a third aspect, the present disclosure provides a process for producing carbon monoxide by hydrogenation and reduction of carbon dioxide, the process comprises contacting a mixed gas of carbon dioxide and hydrogen sequentially with the porous material layer and the molecular sieve layer of the catalyst system, under carbon dioxide hydrogenation and reduction conditions.

In a fourth aspect, the present disclosure further provides a method for enhancing the catalytic activity and/or lifetime of the catalyst during a heterogeneous catalysis process, the method comprises providing and/or replenishing metal active sites in-situ in a catalyst system by means of a metal migration method, the catalyst system is the catalyst system of the first aspect.

Due to the aforementioned technical scheme, the present disclosure has the following advantages:

1. Utilization of the feedstock is higher by increasing the catalyst activity;
2. Reduced deactivation rate lowers the frequency of regeneration, thereby reducing the operating costs of technological process.
3. By providing and/or replenishing metal active sites in-situ, the regeneration performance and lifetime of catalysts can be significantly improved.

DETAILED DESCRIPTION

Figure 1:
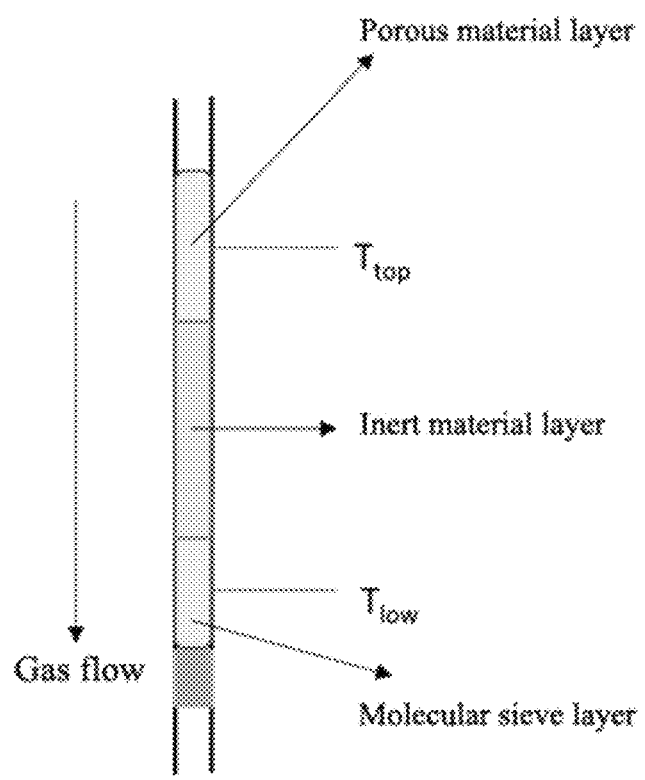
FIG. 1 illustrates a schematic diagram of a catalyst system provided by the present disclosure.
Figure 2:
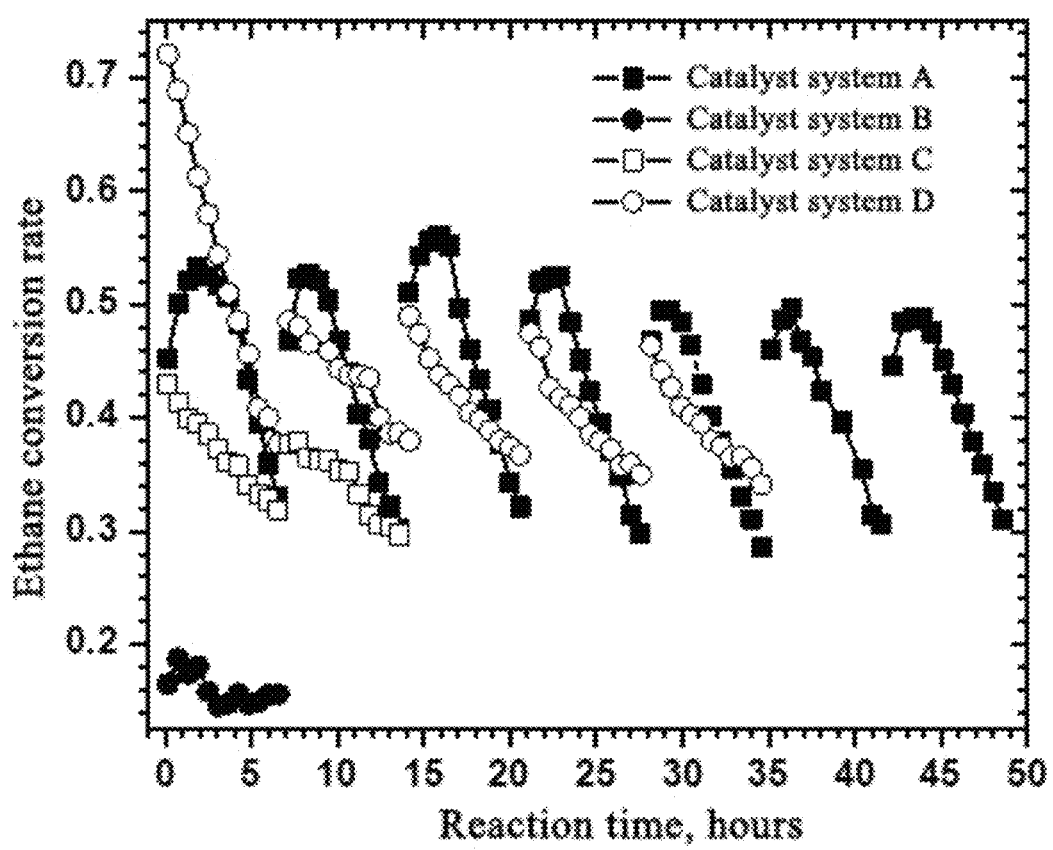
FIG. 2 shows a comparison of the ethane conversion rate in the catalytic performance of catalyst system A with other catalyst systems B, C, D in the ethane aromatization.

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to produce one or more new numerical ranges, which should be deemed have been specifically disclosed herein.

The present disclosure provides a catalyst system comprising at least two layers, wherein at least one layer is a porous material layer containing an active metal component, at least one other layer is a molecular sieve material layer.

The present disclosure does not impose particular limitation to the upper and lower positional relationship between the porous material layer and the molecular sieve layer, and preferably, the porous material layer and the molecular sieve layer are arranged from the top to the bottom in the direction of material flow, that is, the material flow is initially contacted with the porous material layer, and then contacted with the molecular sieve layer.

Preferably, a weight ratio (or a thickness ratio) of the porous material layer containing an active metal component to the molecular sieve layer is 1:0.1-10, preferably 1:0.3-5.

Preferably, in the porous material layer containing an active metal component, the weight ratio of the active metal component to the porous material is 1: 5-1,000, preferably 1:10-100.

In the present disclosure, the active metal component is preferably a metal atom having light hydrocarbon arylation conversion activity or carbon dioxide conversion activity, further preferably one or more selected from the group consisting of Zn, Pt, Ni, Co, Mn, Ti, Ga, Sn, Pd, Rh, Ru, Mo, W, Ir, Au, Ag, Re and Bi.

In the present disclosure, the porous material may be various inert materials having a pore structure and having no adverse effect on the catalyst, for example, it may be various porous inorganic heat-resistant oxides, preferably one or more selected from the group consisting of alumina, silicon oxide, zirconium oxide, titanium oxide, cerium oxide, tungsten oxide and molybdenum oxide.

In the present disclosure, it is preferable that the molecular sieve is a zeolitic molecular sieve having a microporous structure, preferably a zeolitic molecular sieve having a MFI or MEL structure, more preferably one or more selected from the group consisting of ZSM-5, ZSM-8, ZSM-11, ZSM-12, ZSM-23 and ZSM-35.

Preferably, the molecular sieve has a Si/Al molar ratio within a range of 23-400, preferably 30-80.

The molecular sieve layer contains or does not contain a binder, the binder may be present in an amount of 0-40 wt %, preferably 10-40 wt %, and more preferably 20-30 wt %, of the total amount of molecular sieve layer. Preferably, the binder is one or more selected from the group consisting of silica, alumina, silicon carbide, clay, cerium oxide, lanthanum oxide, magnesium oxide, titanium oxide and zirconium oxide.

The molecular sieve layer may contain or does not contain an active metal component. The active metal component may be the same as or different with the active metal component described above, depending on the reaction requirements. The active metal component may be contained in an amount of 0.01-10%, preferably 0.05-2%, based on the weight of said molecular sieve.

Preferably, the catalyst system satisfies that during the reaction process, the active metal component is migrated into the molecular sieve layer and is captured by the molecular sieve in the molecular sieve layer. In the preferred embodiment, the active metal component can be migrated from the porous material layer to the molecular sieve layer and be captured by the molecular sieve in the molecular sieve layer through the metal migration method under the reaction conditions, thereby providing the metal active sites under the in-situ conditions. The catalyst system can delay elution of the active metal component during the catalytic reaction, by providing and/or replenishing metal active sites in-situ to maintain catalytic performance and increase catalyst lifetime.

Preferably, the catalyst system provided by the present disclosure can be used in the hydrocarbon conversion, the porous material layers and molecular sieve layers are respectively disposed upstream and downstream according to the gas flow direction during an application process, the active metal component in said porous material layers is carried to the downstream molecular sieve layers by using a feed material flow or a carrier gas, and is captured by the molecular sieves, so as to maintain the number of accessible active sites during the catalytic reaction.

Although various methods have been used in the prior art to stabilize the active metal component, such as by introducing a second metal in the catalyst or adding a non-metal oxide or sulfide to the feed material, the methods in the prior art have significant limitations and disadvantages. As recited in the background art, the addition of a second metal reduces the catalyst activity and BTX selectivity. The present disclosure provides a catalyst system which can exhibit desirable catalytic activity, stability, renewability and selectivity without involving with an use of a second metal or a non-metal oxide or a sulfide in the feed material, and therefore has significant benefits.

Preferably, the porous material containing an active metal component is prepared through the following method: impregnating the porous material powder with a solution containing a precursor of the active metal component, then calcining the impregnated material in an oxygen-containing atmosphere at 400-700° C., preferably 500-600° C. for 2-6 hours. The oxygen-containing atmosphere is air, for example.

In order to speed up the calcination process and improve the calcination quality, the impregnated material is preferably subjected to rotary evaporation (e.g., by using a rotary evaporator) to remove the solvent. The temperature of rotary evaporation may be within a range of 40-100° C., preferably 60-85° C.

In the present disclosure, the active metal component precursor may be a corresponding soluble metal compound, for example, one or more selected from the group consisting of nitrate and chloride. Preferably, the active metal component precursor is one or more selected from the group consisting of nitrates and/or chlorides of Zn, Pt, Ni, Co, Mn, Ti, Ga, Sn, Pd, Rh, Ru, Mo, W, Ir, Au, Ag, Re and Bi. The solvent forming the solution is preferably water, or a mixed solvent of water and alcohols. Preferably, the solution is one or more selected from the group consisting of nitrate solutions and/or chloride solutions of Zn, Pt, Ni, Co, Mn, Ti, Ga, Sn, Pd, Rh, Ru, Mo, W, Ir, Au, Ag, Re and Bi, for example a zinc nitrate solution, a platinum nitrate solution. The concentration of said solution is preferably 5-25 wt %.

Although the other methods for synthesizing Zn- and Pt-based catalysts by the migration and capture process of metals may have been reported, these methods either utilize complex preparation equipment or require strict treatment conditions. The methods of the present disclosure do not require complex preparation equipment or strict treatment conditions, thus are more beneficial to the practical applications.

The porous material containing the active metal component and the molecular sieve material in the molecular sieve layer of the catalyst system provided by the present disclosure may be in a powder form, or in the shaping form of a clover, strip, column, sphere and the like. For the purpose of facilitating recycling, the catalyst is preferably in the aforementioned shaping form.

According to the present disclosure, it is preferred that the porous material layer and the molecular sieve layer are in direct contact or alternately arranged. That is, the porous material layer and the molecular sieve layer may be separated by a distance, when the distance between the two layers is zero, their relationship is defined as direct contact; when the distance between the two layers is not zero, indicating that the two layers are alternately arranged.

When the porous material layer and the molecular sieve layer are alternately arranged, an inert material layer may be filled or not filled between the porous material layer and the molecular sieve layer, and preferably, a ratio of the distance separating the porous material layer and the molecular sieve layer relative to a thickness of the molecular sieve layer is 0-10:1. The present disclosure is not particularly limited to the particular species of an inert material filled in the inert material layer, as long as the inert material does not involve with reaction and does not adversely affect the reaction.

In a typical embodiment, a dual-layered catalyst system is used for light hydrocarbon arylation. In the catalyst system, a porous material layer containing an active metal component and a molecular sieve layer are disposed at an upper layer and a lower layer, respectively. The upper and lower layers of the dual-layered catalyst system can be disposed in different locations in the same reactor or in different reactors to obtain different reaction temperatures. For example, alumina particles containing an active metal component need to be disposed in an upper part of the reactor or in an upstream reactor, while ZSM-5 particles containing a silica or alumina binder need to be disposed in the lower part of the reactor or in a downstream reactor.

The present disclosure can also provide a metal-modified molecular sieve material having high dispersion and accessibility. The metal comprises one or more selected from the group consisting of Zn, Pt, Ni, Co, Fe, Mn, Ti, Ga, Sn, Pd, Rh, Ru, Mo, W, Ir, Au, Ag, Re and Bi. Zn and Pt are two effective examples. The molecular sieve is a zeolite molecular sieve having a microporous structure, preferably a zeolite molecular sieve having a MFI structure, and more preferably one or more selected from the group consisting of ZSM-5, ZSM-11 and ZSM-12. HZSM-5 is an effective example. The loading amount of metal on the molecular sieve can vary from 0.01 wt % to 10 wt %. The metal-modified molecular sieve material with high dispersion and accessibility is obtained by migration of the metal from a porous material layer to a molecular sieve layer after subjecting the catalyst system to the hydrogen gas processing.

The present disclosure can also provide a method of preparing the aforementioned material, the method comprising the active metal component is migrated into a molecular sieve layer and is captured by the molecular sieve in the molecular sieve layer by means of metal migration method during the reaction process.

The present disclosure may further provide a catalyst prepared with the above method, the catalyst can be used for a conversion of hydrocarbons and a conversion of carbon dioxide; wherein the conversion of hydrocarbons includes one or more selected from the group consisting of aromatization, dealkylation, alkylation, dehydrogenation and hydrogenation. The conversion of carbon dioxide includes one or more selected from the group consisting of conversion to carbon monoxide, conversion to hydrocarbons, and conversion to alcohols.

The present disclosure provides a light hydrocarbon aromatization method, the method comprises sequentially contacting the light hydrocarbons with the porous material layer and the molecular sieve layer of the catalyst system under the light hydrocarbon aromatization conditions.

Preferably, the aromatization of the light hydrocarbons is performed under the reducing environments.

Preferably, the light hydrocarbon aromatization conditions comprise a pressure of 0.01-2 MPa on a gauge pressure basis; a temperature of 300° C.-700° C., preferably 400° C.-650° C.; and a volumetric hourly space velocity of light hydrocarbons being 500 $h^{-1}$-50,000 $h^{-1}$, preferably 1,000 $h^{-1}$-10,000 $h^{-1}$.

Wherein the preferred conditions of contacting with the porous material layer comprise a pressure of 0.01-2 MPa on a gauge pressure basis; a temperature of 300° C.-700° C., preferably 400° C.-600° C.; and a volumetric hourly space velocity of light hydrocarbons being 500 $h^{-1}$-50,000$h^{-1}$, preferably 1,000 $h^{-1}$-10,000 $h^{-1}$.

Wherein the preferred conditions of contacting with the molecular sieve layer comprise a pressure of 0.01-2 MPa on a gauge pressure basis; a temperature of 300° C.-700° C., preferably 500° C.-650° C.; and a volumetric hourly space velocity of light hydrocarbons being 500 $h^{-1}$-50,000 $h^{-1}$, preferably 1,000 $h^{-1}$-10,000 $h^{-1}$.

Preferably, said contacting is carried out in a fixed bed reactor, a fluidized bed reactor or a moving bed reactor.

The method of the present disclosure is applicable to a wide variety of hydrocarbon materials capable of performing dehydrogenation reaction and carrying out oligomerization/aromatization reaction to produce aromatic hydrocarbons, preferably the light hydrocarbons are alkanes having not more than 5 carbon atoms, such as methane, ethane, propane, butane, pentane and various isomers thereof. Preferably, the content of ethane in the light hydrocarbons is not lower than 65 wt %, preferably 75-100 wt %.

The present disclosure further provides a process for producing carbon monoxide by hydrogenation and reduction of carbon dioxide, the process comprises contacting a mixed gas of carbon dioxide and hydrogen sequentially with a porous material layer and a molecular sieve layer of the catalyst system, under the carbon dioxide hydrogenation and reduction conditions. Preferably, the mixed gas has a volume ratio of carbon dioxide to hydrogen in the range of 1:1 to 1:4.

The present disclosure has a wide selection scope in regard to the carbon dioxide hydrogenation and reduction conditions. Preferably, said carbon dioxide hydrogenation and reduction conditions comprise: a temperature of 200-650° C., a pressure of 0.01-5 MPa, and the mixed gas has a volumetric hourly space velocity of 500-50,000 $h^{-1}$.

The present disclosure further provides a method for enhancing the catalytic activity and/or lifetime of the catalyst during a heterogeneous catalysis process, the method comprises providing and/or replenishing metal active sites in-situ in a catalyst system by means of a metal migration method, the catalyst system is the catalyst system of the first aspect.

Preferably, the metal migration method comprises that the active metal component is migrated into a molecular sieve layer, and is captured by a molecular sieve in the molecular sieve layer during the reaction process, thereby providing in-situ and/or replenishing metal active sites during the reaction process.

Preferably, the method of metal migration comprises: initially impregnating the porous material powder with a solution containing a precursor of the active metal component, then calcining the impregnated material in an oxygen-containing atmosphere at 400-700° C., preferably 500-600° C. for 2-6 hours. The optional range of the solution is the same as that of the aforesaid active metal component precursor, wherein the active metal component may be same as or different from the aforesaid active metal component. The optional range of the porous material is same as that of the aforesaid porous material. The active metal component in the porous material layer is then carried by using a feed material flow or a carrier gas to a downstream molecular sieve layer during the reaction process, and is captured by the molecular sieve, in order to provide and/or replenish metal active sites in-situ during the catalytic reaction process.

The present disclosure is not particularly limited to the conditions of metal migration, as long as it enables migration of the active metal component in the upper layer of porous material layer to the molecular sieve layer in the catalyst system.

Preferably, the metal migration method is performed in a hydrogen-containing atmosphere (hydrogen gas is preferred), preferably performed under the conditions consisting of a temperature of 500-700° C., a pressure of 0.01-2 MPa, and a hydrogen flow rate of 10-200 sccm.

Preferably, the metal migration method is performed under the light hydrocarbon aromatization conditions, or carbon dioxide hydrogenation and reduction conditions. In the preferred embodiment, there is migration of metal in the catalyst system during the process of light hydrocarbon arylation conversion reaction or carbon dioxide hydrogenation reaction, it is more conducive to improving activity and stability of the catalyst.

The light hydrocarbon aromatization conditions and the carbon dioxide hydrogenation and reduction conditions are as described above and will not be repeatedly described herein. It shall be noted that the light hydrocarbon aromatization conditions may include, in addition to the aforementioned light hydrocarbon aromatization conditions, the conditions of air regeneration performed after completion of the reaction, that is, metal migration does not occur alone during the light hydrocarbon aromatization reaction process, but occurs during both the light hydrocarbon aromatization reaction process and the air regeneration process. The present disclosure does not impose specific limitation to the air regeneration conditions, e.g., the air regeneration may be performed under an air atmosphere at a temperature of 500-800° C. for 1-10 hours.

The present disclosure will be described below in detail with reference to examples. In the following examples, the content of Pt and Zn in the catalyst was measured by using an X-ray fluorescence spectrometer through an X-ray fluorescence spectroscopy method.

Example 1

5 g of $Al_2O_3$ powder was mixed with a certain amount of $Zn(NO_3)_2$ solution (the loading amount of Zn was 4 wt % based on $Al_2O_3$), and sufficiently impregnated at room temperature for 1 hour, followed by rotary evaporation at 80° C. with a rotary evaporator to obtain a solid product, which was subjected to calcination in air at 550° C. for 4 hours. The powder was then pressed and sieved to obtain a 20×40 mesh product. 1 g of the above product was placed in the upper part of a reaction tube having an inner diameter of 9 mm of a quartz reactor.

5 g of HZSM-5 powder with a Si/Al ratio of 30 was physically mixed with an $Al_2O_3$ binder (at a weight ratio of 70:30), the mixture was subsequently pressed and sieved to obtain a 20×40 mesh product. 1 g of the product was placed in a lower part of the reaction tube.

The upper part and the lower part were spaced apart with a silica wool (a thickness ratio of the silica wool to the product in the lower part was 1:0.5), the obtained reaction system was named as the catalyst system A. The structure schematic diagram of the reaction system was shown in FIG. 1. $T_{top}$ denoted the temperature of said upper layer and $T_{low}$ denoted the temperature of said lower layer. $T_{top}$ was comparable to $T_{low}$ throughout the technological process.

1 g of the pressed and sieved HZSM-5 was placed in a reactor tube, and named as the catalyst system B.

5 g of ZSM-5 powder (with a Si/Al ratio of 30) was mixed with a certain amount of $Zn(NO_3)_2$ solution (the loading amount of Zn was 1 wt % based on ZSM-5), and sufficiently impregnated at room temperature for 1 hour, followed by rotary evaporation at 80° C. with a rotary evaporator to obtain a solid product, which was subjected to calcination in air at 550° C. for 4 hours. The powder was physically mixed with an $Al_2O_3$ binder (at a weight ratio of 70:30), the mixture was subsequently pressed and sieved to obtain a 20×40 mesh product. 1 g of the product was placed in a reaction tube. The obtained reaction system was named as the catalyst system C.

5 g of ZSM-5 powder (with a Si/Al ratio of 30) was mixed with a certain amount of $Zn(NO_3)_2$ solution (the loading amount of Zn was 4 wt % based on ZSM-5), and sufficiently impregnated at room temperature for 1 hour, followed by rotary evaporation at 80° C. with a rotary evaporator to obtain a solid product, which was subjected to calcination in air at 550° C. for 4 hours. The powder was physically mixed with an $Al_2O_3$ binder (at a weight ratio of 70:30), the mixture was subsequently pressed and sieved to obtain a 20×40 mesh product. 1 g of the product was placed in a reaction tube. The obtained reaction system was named as the catalyst system D.

1 g of the pressed and sieved $Al_2O_3$ containing Zn in an amount of 4 wt % (i.e. an upper layer of catalyst system A) was placed in a reactor tube, the obtained reaction system was named as the catalyst system E.

Example 2

5 g of $Al_2O_3$ powder was mixed with a certain amount of $Pt(NO_3)_2$ solution (the loading amount of Pt was 0.5 wt % based on $Al_2O_3$), and sufficiently impregnated at room temperature for 1 hour, followed by rotary evaporation at 80° C. with a rotary evaporator to obtain a solid product, which was subjected to calcination in air at 550° C. for 4 hours. The powder was then pressed and sieved to obtain a 20×40 mesh product. 0.3 g of the above product was placed in the upper part of a reaction tube.

5 g of ZSM-5 powder with a Si/Al ratio of 30 was mixed with a certain amount of $Pt(NO_3)_2$ solution (the loading amount of Pt was 500 ppm based on ZSM-5), and sufficiently impregnated at room temperature for 1 hour, followed by rotary evaporation at 80° C. with a rotary evaporator to obtain a solid product, which was subjected to calcination in air at 550° C. for 4 hours. The powder was then physically mixed with an $Al_2O_3$ binder (at a weight ratio of 70:30), the mixture was subsequently pressed and sieved to obtain a 20×40 mesh product. 1 g of the product was placed in a lower part of the reaction tube.

The upper part and the lower part were spaced apart with a silica wool (a thickness ratio of the silica wool to the product in the lower part was 1:5), the obtained reaction system was named as the catalyst system F.

1 g of the pressed and sieved HZSM-5 containing 500 ppm of Pt was placed in a reactor tube, the obtained reaction system was named as the catalyst system G.

0.3 g of the pressed and sieved $Al_2O_3$ containing 0.5 wt % of Pt was placed in the reactor tube, the obtained reaction system was named as the catalyst system H.

TABLE 1

| Catalyst system | Upper layer | Lower layer | Weight ratio of upper layer to lower layer |
| --- | --- | --- | --- |
| A | $Al_2O_3$ + Zn (4%), subjected to calcination at 550° C. for 4 hours | HZSM-5 (with a Si/Al ratio of 30) + $Al_2O_3$ binder (70:30) | 1:1 |
| B | HZSM-5 (with a Si/Al ratio of 30) + $Al_2O_3$ binder (70:30) | | / |
| C | ZSM-5 + Zn(1%) + $Al_2O_3$ binder (70:30), subjected to calcination at 550° C. for 4 hours | | / |
| D | ZSM-5 + Zn(4%) + $Al_2O_3$ binder (70:30), subjected to calcination at 550° C. for 4 hours | | / |
| E | $Al_2O_3$ + Zn(4%), subjected to calcination at 550° C. for 4 hours | | / |
| F | $Al_2O_3$ + Pt (0.5%), subjected to calcination at 550° C. for 4 hours | ZSM-5 (with a Si/Al ratio of 30) + Pt(500 ppm) + $Al_2O_3$ binder (70:30) | 0.3:1 |
| G | HZSM-5(with a Si/Al ratio of 30) + Pt(500 ppm) + $Al_2O_3$ binder (70:30) | | / |
| H | $Al_2O_3$ + Pt(0.5%), subjected to calcination at 550° C. for 4 hours | | / |

Catalyst Performance Evaluation

The catalyst systems were respectively used to carry out the low-carbon hydrocarbon aromatization reaction, the specific operations were as follows:

(1) $H_2$ with a flow rate of 66.7 sccm was introduced into the reactor at an atmospheric pressure, the reactor was heated to 630° C. at a temperature rise rate of 15° C./min, and then kept at the temperature for 60 minutes to perform preheating;

(2) A mixture gas of $C_2H_6/N_2$ ($N_2$ was used as an interior standard gas) with a volume ratio of 1.67:1 was supplied into the reactor as a feed material. The reaction temperature was set at 630° C., the Weight Hourly Space Velocity (WHSV) of $C_2H_6$ was 1,000 $h^{-1}$, and the pressure was atmospheric pressure.

(3) The catalyst was subjected to regeneration treatment after 7 hours of the continuous reaction, the specific operations were as follows: the catalyst was heated to 550° C. at a temperature rise rate of 2° C./min under an air atmosphere, and the temperature was kept for 4 hours. The catalyst was subsequently used for the lower carbon hydrocarbon aromatization reaction. In such a way, one cycle was completed.

Wherein the catalyst system A was subjected to 7 cycles, the catalyst system B was subjected to 1 cycle, the catalyst system C was subjected to 2 cycles, and the catalyst system D was subjected to 5 cycles.

The composition of the product stream was analyzed on-line by the Gas Chromatography (GC).

Figure 3:
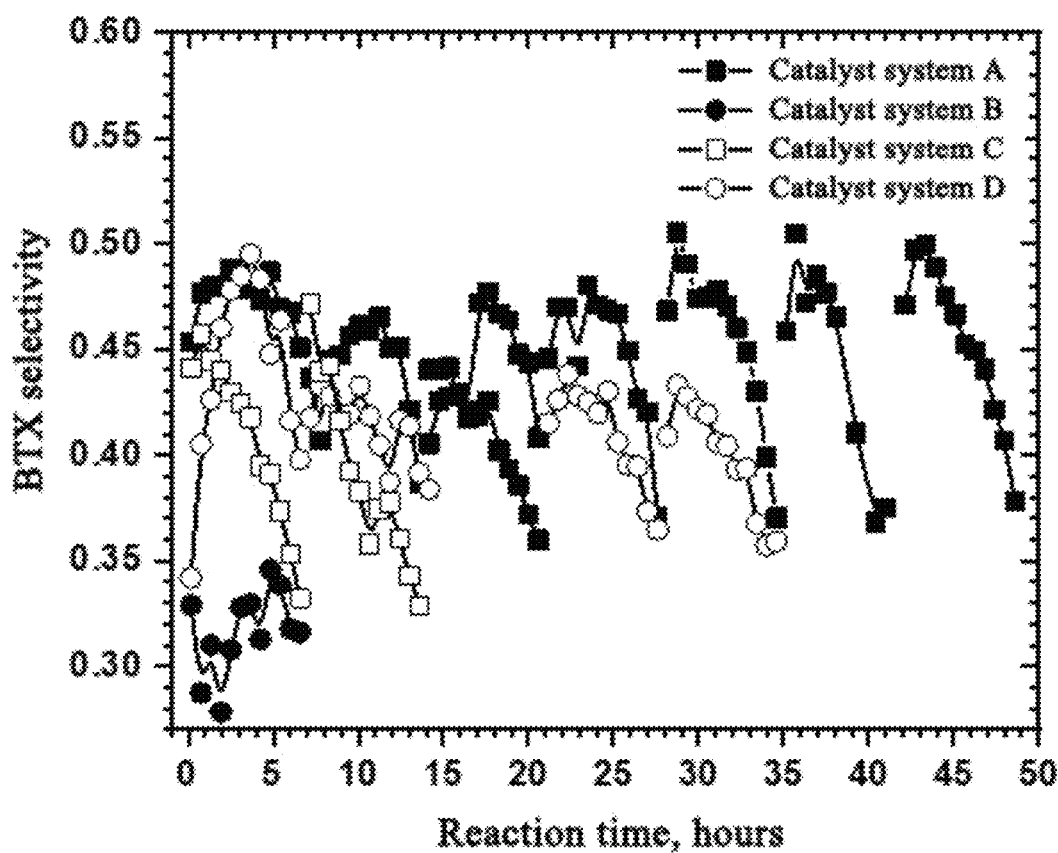
FIG. 3 shows a comparison of the BTX selectivity in the catalytic performance of catalyst system A with other catalyst systems B, C, D in the ethane aromatization.
Figure 4:
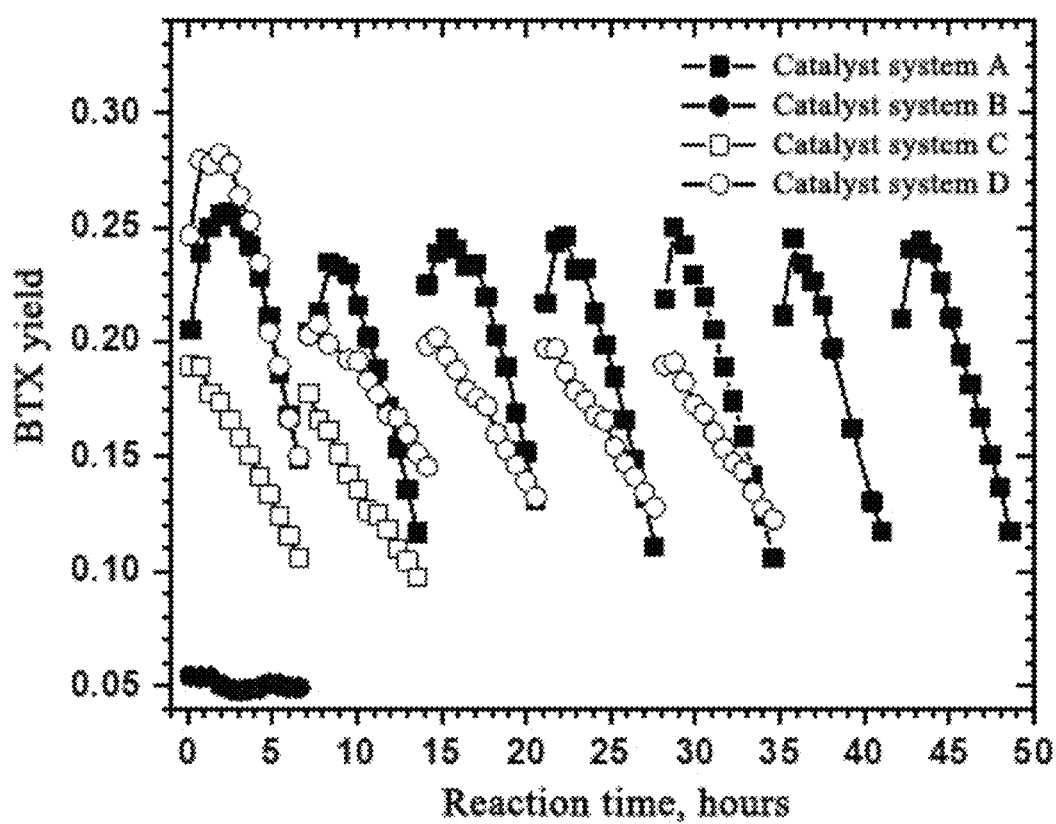
FIG. 4 shows a comparison of the BTX yields in the catalytic performance of catalyst system A with other catalyst systems B, C, D in the ethane aromatization.

The results were shown in FIG. 2 through FIG. 6. As can be seen from FIG. 2, the activity of catalyst system B was too low, the catalyst system C had low BTX selectivity and yield, the cycle regeneration performance of the catalyst system D was significantly inferior to the catalyst system A. FIG. 3 illustrated that the catalyst system A had an obviously higher BTX selectivity than other catalyst systems, especially after multiple cycles. FIG. 4 illustrated that the catalyst system A had an obviously higher BTX yield than other catalyst systems, especially after multiple cycles.

The catalyst system E formed only a negligible amount of BTX, indicating that Zn-loaded $Al_2O_3$ was not active in the ethane aromatization. Therefore, in the catalyst system A, only Zn component loaded in HZSM-5 participated in the ethane aromatization.

The catalyst system A showed much better catalytic performance, catalyst stability and regenerability in the ethane aromatization than the catalyst system C. After the reaction, the amount of Zn on HZSM-5 in catalyst system A was very similar with that in the catalyst system C. Thus, Zn/ZSM-5 prepared by the migration method had higher catalytic activity than Zn/ZSM-5 prepared by the wet impregnation method.

The catalyst system A exhibited better catalyst stability and regenerability in the ethane aromatization than the catalyst system D. The total used amount of Zn in the catalyst system A was the same as that in the catalyst system D. Therefore, Zn/ZSM-5 prepared by the migration method also had much higher catalyst stability and longer catalyst lifetime than Zn/ZSM-5 prepared by the wet impregnation method.

Figure 5:
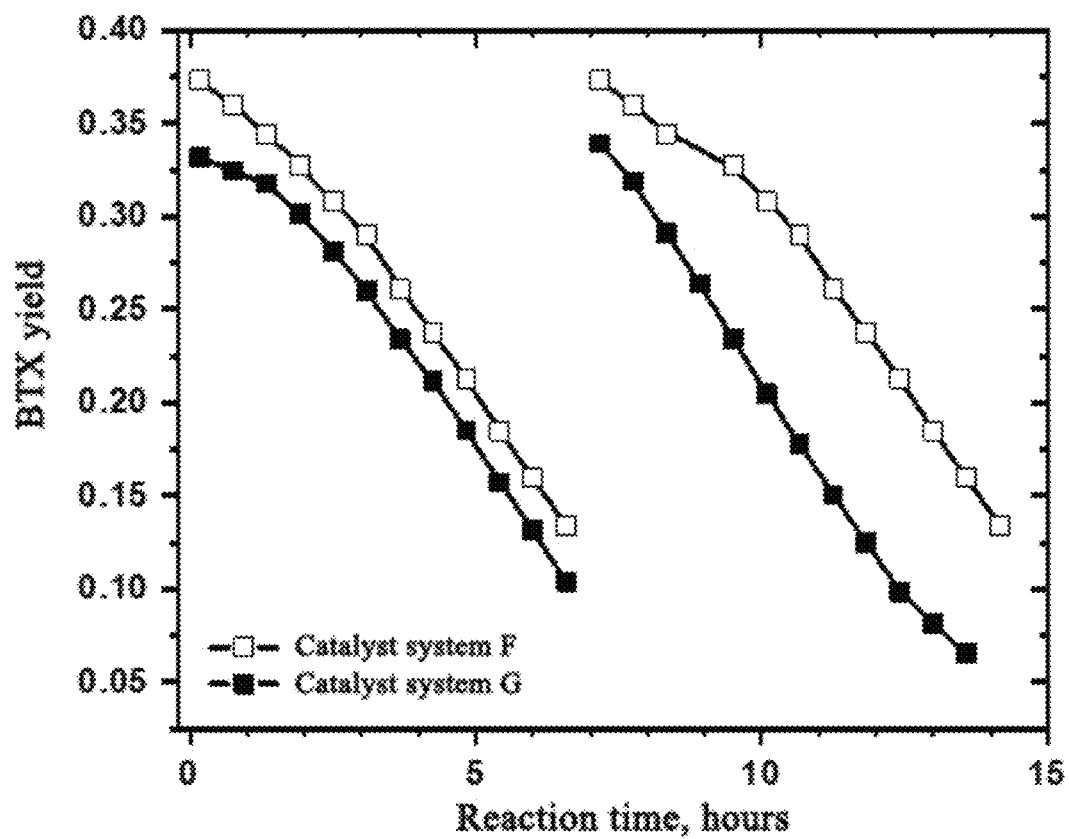
FIG. 5 shows a comparison of the BTX yields in the catalytic performance between the catalyst system F and the catalyst system G disclosed in the ethane aromatization.

FIG. 5 showed a comparison of catalytic performance in an aspect of BTX yield between the catalyst system F and the catalyst system G disclosed in the ethane aromatization. Wherein both the catalyst system F and the catalyst system G were run for 2 cycles. It was clearly shown in FIG. 5 that in the second cycle data, the catalyst system F showed better catalytic performance, catalyst stability and regenerability in the ethane aromatization than the catalyst system G in which only Pt/HZSM-5 was used.

Figure 6:
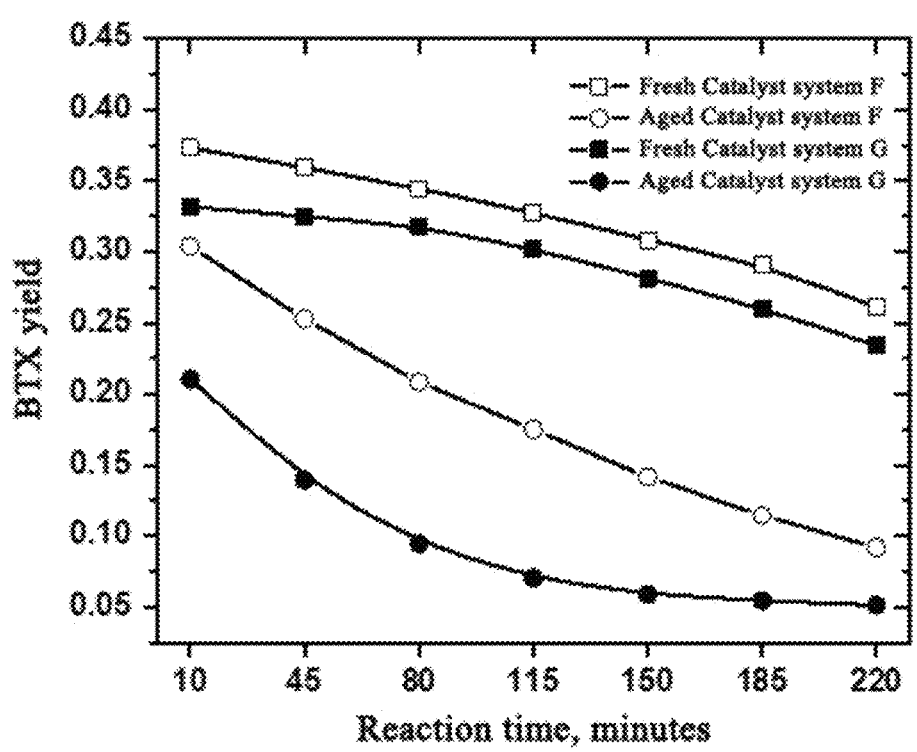
FIG. 6 shows a comparison of catalytic performance in terms of BTX yield between the disclosed catalyst system F and catalyst system G, and the performance of the aged catalyst system F and the aged catalyst system G after six repeated cycles of air and hydrogen treatment.

FIG. 6 showed a comparison of catalytic performance in terms of BTX yield between the disclosed catalyst system F and catalyst system G, and the performance of the aged catalyst system F and the aged catalyst system G after six repeated cycles of air and hydrogen treatment. The catalyst was initially treated with air at 550° C. for 1 hour and then treated with hydrogen gas at 630° C. for 1 hour, such a process was referred to as one cycle of treatment with air and hydrogen gas. FIG. 6 showed that the cyclic treatment with air and hydrogen gas may significantly reduce activity of Pt-based catalysts in the ethane aromatization. The cyclic treatment can be used for simulating the aging process of Pt-based catalysts in light alkane aromatization.

FIG. 6 also demonstrated that after a similar aging process, the catalyst system F again exhibited better performance than the catalyst system G.

The test results also showed that the catalyst system H only using Pt/$Al_2O_3$ merely formed a negligible amount of BTX, indicating that the Pt-loaded $Al_2O_3$ was not active in the ethane aromatization Thus, in the catalyst system F, only Pt component loaded in HZSM-5 participated in the ethane aromatization.

The catalyst system F had better catalytic performance than the catalyst system G, indicating that the Pt component, which migrated from $Al_2O_3$ to ZSM-5, was also active for the ethane aromatization. More importantly, the Pt component provided in-situ can improve the catalyst stability and regenerability of Pt-based catalysts in the ethane aromatization.

The following examples were provided to illustrate the metal migration process of the present disclosure.

Example 3

5 g of the HZSM-5 powder with a Si/Al ratio of 30 was physically mixed with an $Al_2O_3$ binder (at a weight ratio of 70:30), the mixture was then pressed and sieved to obtain a 20×40 mesh product. 0.3 g of the product was placed in a reaction tube. And 0.3 g of the pressed and sieved $Al_2O_3$ containing 0.5 wt % Pt was placed directly above HZSM-5. In the meanwhile, the $Al_2O_3$ layer and the HZSM-5 layer had the same temperature. They were then treated with various gases. The post-treatment characterization results (EDX, XRD and dynamic CO chemisorption) showed that Pt was not present in the HZSM-5 layer after treatment with an inert gas (nitrogen gas) at 550° C. or 630° C. for 1 hour, indicating that Pt was not migrated from $Al_2O_3$ to HZSM-5 by treatment with an inert gas. However, for the case where the catalyst was initially treated with air at 550° C. for 1 hour and then treated with hydrogen gas at 630° C. for 1 hour, there was some Pt in the HZSM-5 layer, indicating that there was migration of Pt from $Al_2O_3$ to HZSM-5 after the catalyst was treated with air at 550° C. and then treated with hydrogen gas at 630° C. Furthermore, it was found that more significant Pt migration occurred after several cycles of treatment with the aforementioned air+hydrogen gas treatment conditions (the catalyst was initially treated with air at 550° C. for 1 hour and then treated with hydrogen gas at 630° C. for 1 hour, the air+hydrogen gas treatment process was performed in a cycle).

Example 4

5 g of powder was mixed with a certain amount of $Zn(NO_3)_2$ solution (the loading amount of Zn was 10 wt % based on $Al_2O_3$), and impregnated at room temperature for 1 hour, followed by rotary evaporation at 80° C. with a rotary evaporator to obtain a solid product, which was subjected to calcination in air at 550° C. for 4 hours. The powder was then pressed and sieved to obtain a 20×40 mesh product. 0.5 g of 10 wt % $Zn/Al_2O_3$ was placed in the upper part of the reaction tube.

0.5 g of ZSM-5 containing 30 wt % of $Al_2O_3$ binder (with a Si/Al ratio of 30) was placed in the lower part of the reaction tube.

The upper part and the lower part were spaced apart by a silica wool (a thickness ratio of silica wool to the product in the lower part was 1:0.5), the structure schematic diagram of the reaction system was shown in FIG. 1. Moreover, in the example, the temperature $T_{top}$ in the upper part and the temperature $T_{low}$ in the lower part were similar.

Various gas treatments were then carried out in the reaction system. In an experiment (1), the system was treated with air at a temperature of 600° C. for 9 hours at a flow rate of 100 sccm. In experiment (2), the system was treated with nitrogen gas at a temperature of 600° C. for 9 hours at a flow rate of 100 sccm. In experiment (3), the system was treated with hydrogen gas at a temperature of 600° C. for 9 hours at a flow rate of 100 sccm. In experiment (4), the system was treated with hydrogen gas at a temperature of 600° C. for 9 hours at a flow rate of 20 sem. In each experiment, after the treatment with gas, the 1 wt % $Zn/Al_2O_3$ in the upper part and ZSM-5 in the lower part were separated and characterized by various technical means including XRF, XRD, and dynamic CO chemisorption. Table 2 showed the loading amount of Zn on $Al_2O_3$ (wt %) before the gas treatment and after the gas treatment, as well as the approximate percentage of Zn migrated from the $Al_2O_3$ carrier.

TABLE 2

Various gas treatment results (600° C., 9 h) for 10 wt % $Zn/Al_2O_3$

| Samples | Gas flow rate (sccm) | Loading amount of Zn on $Al_2O_3$ (wt %) | Percentage of Zn migrated from the $Al_2O_3$ carrier |
|---|---|---|---|
| $Zn/Al_2O_3$ before the gas treatment | | 10.296 | |
| $Zn/Al_2O_3$, air | 100 | 10.344 | ~0% |
| $Zn/Al_2O_3$, nitrogen gas | 100 | 10.312 | ~0% |
| $Zn/Al_2O_3$, hydrogen gas | 100 | 9.43 | 8.41% |
| $Zn/Al_2O_3$, hydrogen gas | 20 | 9.611 | 6.65% |

Table 2 clearly demonstrated that there was no Zn migration occurred in the $Al_2O_3$ carrier after 9 hours of treatment with air or nitrogen gas at 600° C. Meanwhile, Zn significantly migrated from the $Al_2O_3$ carrier after 9 hours of treatment with hydrogen gas at 600° C. In other words, the hydrogen gas flow had an influence on promoting migration of Zn, while the oxygen gas flow and the nitrogen gas flow had little effect on promoting migration of Zn.

Furthermore, Table 2 also illustrated that the hydrogen gas flow rate will influence the migration percentage. The hydrogen gas with a flowrate of 100 sccm resulted in 8.40 Zn migrated from the $Al_2O_3$ carrier, while the hydrogen gas with a flow rate of 20 sccm resulted in 6.7 Zn migrated from the $Al_2O_3$ carrier. Therefore, a high flow rate of hydrogen gas was conducive to the migration of Zn.

Example 5

The inventors of the present disclosure further studied the detailed conditions of Zn migration from a silica carrier. The 10 at % $Zn/SiO_2$ carrier was synthesized using a method similar to that of 10 wt % $Zn/Al_2O_3$. Following the method of Example 4, the same gas treatment and the same characterization means were applied to the 10 wt % $Zn/SiO_2$ carrier as in the case of 10 wt % $Zn/Al_2O_3$. The results were shown in Table 3.

TABLE 3

Various gas treatment results (600° C., 9 h) for 10 wt % $Zn/SiO_2$

| Samples | Gas flow rate (sccm) | Loading amount of Zn on $SiO_2$ (wt %) | Percentage of Zn migrated from the $SiO_2$ carrier |
|---|---|---|---|
| $Zn/SiO_2$ before the gas treatment | | 10.338 | |
| $Zn/SiO_2$, air | 100 | 10.191 | 0.386% |
| $Zn/SiO_2$, nitrogen gas | 100 | 10.246 | 0.290% |
| $Zn/SiO_2$, hydrogen gas | 100 | 2.089 | 79.79% |
| $Zn/SiO_2$, hydrogen gas | 50 | 3.032 | 70.67% |
| $Zn/SiO_2$, hydrogen gas | 20 | 6.293 | 39.13% |

Table 3 illustrated the loading weights of Zn on $SiO_2$ before the gas treatment and after the gas treatment, as well as the percentage of Zn migrated from the $SiO_2$ carrier. It was clear that there was no significant Zn migration occurred in the $SiO_2$ carrier after 9 hours of treatment with air or nitrogen gas at 600° C. However, when treated with 100 sccm of hydrogen gas, there was a significant amount of Zn, about 80% of Zn, can migrate from the $SiO_2$ carrier. Furthermore, the percentage of Zn that can migrate from the $SiO_2$ carrier was ~71% and ~39% for the treatment of hydrogen gas at a flow rate of 50 sccm and 20 sccm, respectively. The characterization using an $Al_2O_3$ carrier and a $SiO_2$ carrier clearly indicated that an increased flow rate of the hydrogen gas resulted in more significant migration of Zn. The Zn component located on the $SiO_2$ carrier can migrate from the carrier more easily than the $Al_2O_3$ carrier.

A time series study was also conducted on 10 wt % $Zn/SiO_2$ samples in order to establish a model of the Zn migration velocity under the hydrogen gas flow. For this purpose, three temperatures (500° C., 550° C., 600° C.) were selected for the study, and the other conditions were kept constant in these experiments (0.5 g sample, atmospheric pressure, $H_2$ with a flow rate of 12.5 sccm). The zinc concentration was measured by XRF measurement after each treatment, and the data after 10 h, 20 h, 30 h and 60 hours of treatment with hydrogen gas were collected.

Figure 7:
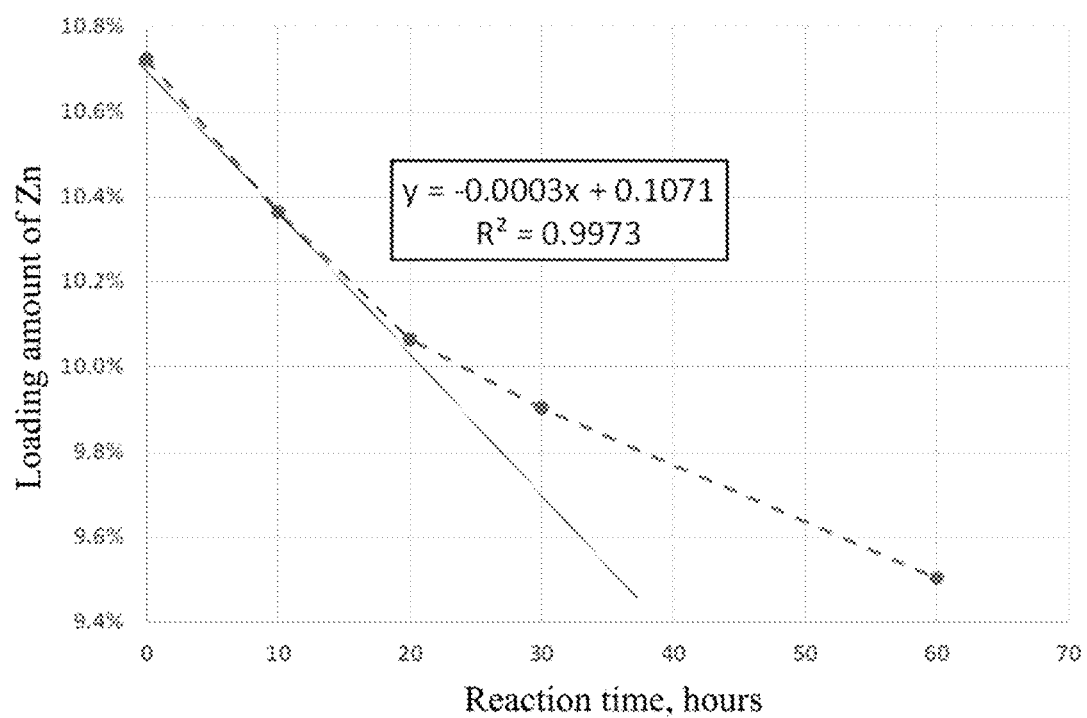
FIG. 7 illustrates a curve graph of Zn loading amount in the catalyst system of Example 5 varies with processing time under the treatment of hydrogen gas at 500° C.

The time series data for a temperature of 500° C. was listed in FIG. 7. Following treatment with hydrogen gas at 500° C., the migration percentage of Zn from the $SiO_2$ carrier was quite low. After 30 hours of treatment with hydrogen gas, the percentage of Zn that can migrate from the $SiO_2$ carrier was 0.82%, which was increased to 1.22% after 60 hours of treatment with hydrogen gas. The migration velocity of Zn was relatively linear over the first 20 hours. Fitting the data of the first 20 hours with a trend line to obtain an equation, which can be used for determining the migration percentage of Zn following treatment with hydrogen gas at 500° C. The data fitting with the trend line obtained a value 0.9973 of R2, indicating a high degree of linearity. In terms of slope, the migration velocity of Zn from 10 wt % $Zn/SiO_2$ was about 0.033 wt %/hour for the first 20 hours of treatment with $H_2$ at 500° C.

Figure 8:
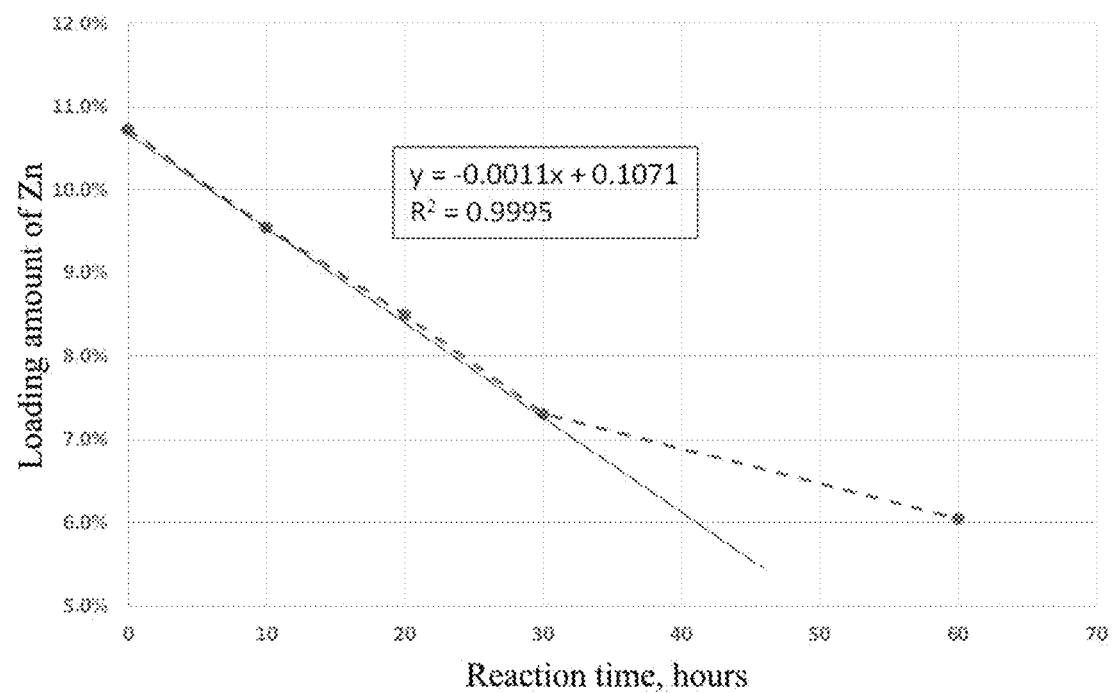
FIG. 8 illustrates a curve graph of Zn loading amount in the catalyst system of Example 5 varies with processing time under the treatment of hydrogen gas at 550° C.

The time series data for a temperature of 550° C. was listed in FIG. 8. As can be seen from FIG. 8, the migration velocity of Zn from the $SiO_2$ carrier during the first 30 hours of treatment followed a linear trend. Fitting the data of the first 30 hours with a trend line to obtain an equation, which can be used for determining the migration percentage of Zn following treatment with hydrogen gas at 550° C. A conclusion can be drawn from a slope of the equation that the migration velocity of Zn from the $SiO_2$ carrier was 0.11 wt %/hour. The value of R2 herein was 0.9995, indicating a high degree of linearity.

Figure 9:
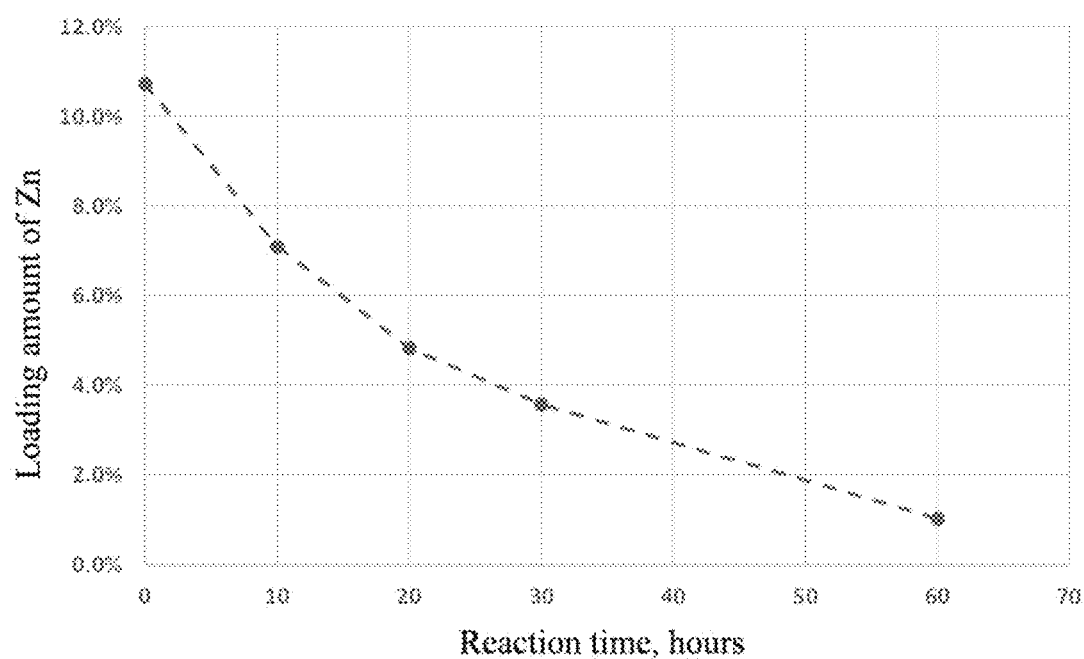
FIG. 9 illustrates a curve graph of Zn loading amount in the catalyst system of Example 5 varies with processing time under the treatment of hydrogen gas at 600° C.

The time series data for a temperature of 600° C. was listed in FIG. 9. It was apparent that the high temperature treatment had a more significant influence on the migration of Zn. After treatment for 60 hours, approximately 90% of Zn migrated from the $SiO_2$ carrier at 600° C., and approximately 44% of Zn migrated from the $SiO_2$ carrier at 550° C. Moreover, the trend line at 600° C. was also significantly different from the trend lines at 500° C. and 550° C., the trend line cannot fit a linear trend.

Furthermore, results on the absence of using silica wool between the ZSM-5 layer and the $Zn/SiO_2$ layer showed that the same Zn migration tendency was observed after hydrogen treatment under these temperatures. In other words, an use of silica wool between the ZSM-5 layer and the Zn source layer merely served to favorably separate the two layers, an existence of said silica wool neither affected the Zn migration velocity nor influenced the catalytic performance of said system.

Example 6

The example served to illustrate the enhancement of catalyst lifetime by providing and/or replenishing metal active sites in-situ through the metal migration methods.

Figure 10:
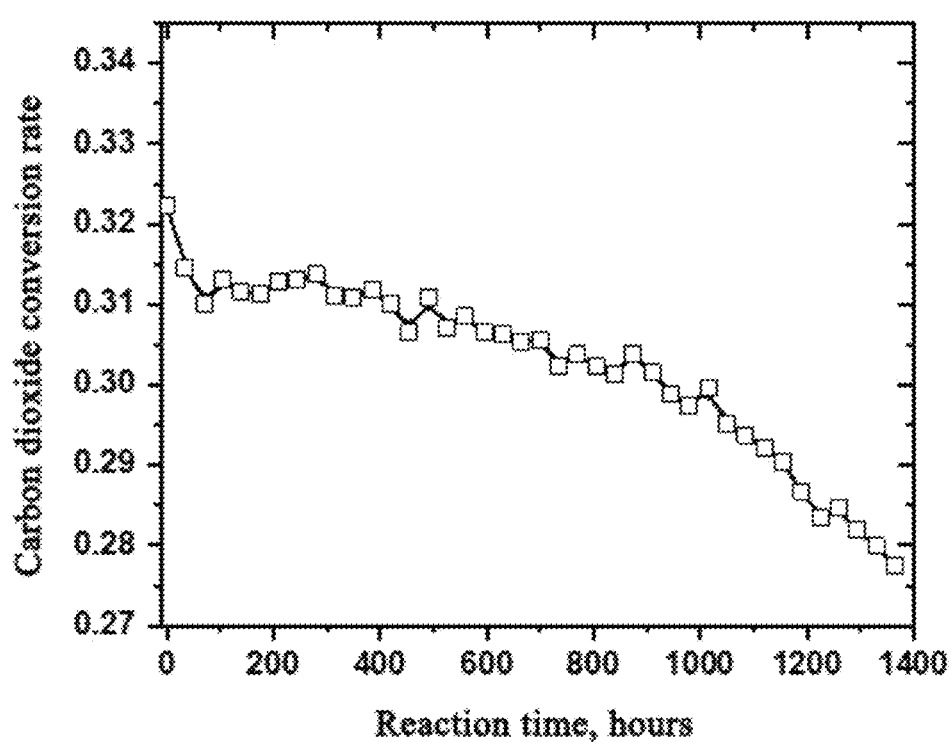
FIG. 10 illustrates the functional relationship between the catalyst stability and the reaction time of 4 wt % Zn/ZSM-5 at 600° C.

The enhancement of catalyst lifetime by providing and/or replenishing metal active sites in-situ through the metal migration methods has been demonstrated in the Reverse Water Gas Shift (RWGS) reaction. In this experiment, the catalytic performance of 4 wt % Zn/ZSM-5 was initially tested in the RWGS reaction. FIG. 10 illustrated the functional relationship between the catalyst stability and the reaction time of 4 wt % Zn/ZSM-5 at 600° C. Reaction conditions were 0.5 g catalyst, $H_2$ with a flow rate of 30 sccm, $CO_2$ with a flow rate of 10 sccm. Catalyst activity appeared to decrease continuously along with an increasing reaction time. The decrease in catalyst activity may result from the loss of active Zn component at high reaction temperature, it was demonstrated by XRF measurement of the samples after the reaction.

Example 7

Figure 11:
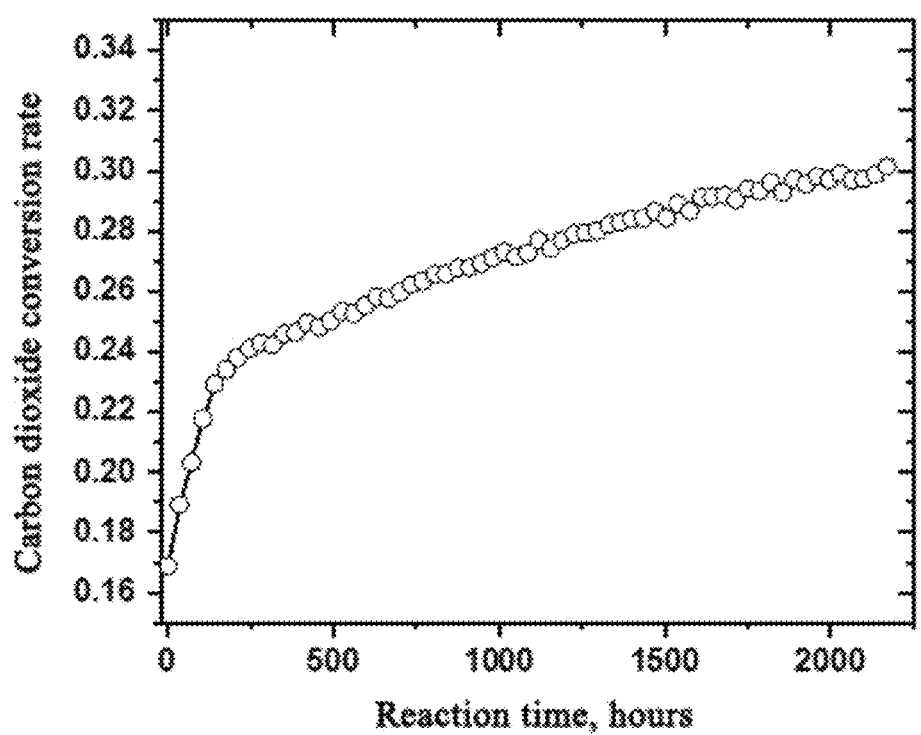
FIG. 11 illustrates a curve graph of carbon dioxide conversion rate varies over time in the catalyst system of Example 7.

In order to demonstrate the improvement of catalyst lifetime by the metal migration method, we also used a two-layer catalyst system in the RWGS reaction. In the upper layer, 0.5 g of 10 wt % $Zn/SiO_2$ was used, while in the lower layer, 0.5 g of ZSM-5 (with a Si/Al ratio of 30) was used, the reaction conditions including a temperature of 600° C., normal pressure, $H_2$ with a flow rate of 30 sccm, $CO_2$ with a flow rate of 10 sccm. The upper and lower layers were separated by silica wool. The temperature $T_{top}$ of said upper layer was similar to the temperature $T_{low}$ of said lower layer. The results were shown in FIG. 11, the stability of such a two-layer system in the RWGS reaction was very desirable. It was indeed observed that there was no decrease in activity, but rather that there was a sustained increase in activity. The increased activity probably derived from the continuous migration of Zn from the $SiO_2$ carrier to the ZSM-5 carrier. Furthermore, when the $Zn/SiO_2$ was used alone, the catalytic activity of 10 wt % $Zn/SiO_2$ on the RGWS reaction was not observed at 600° C. The data clearly demonstrated that the metal migration method can also be used to catalyze $CO_2$ conversion to improve lifetime and stability of the catalyst.

The above content describes in detail the preferred embodiments of the present disclosure, but the present disclosure is not limited thereto. A variety of simple modifications can be made in regard to the technical solutions of the present disclosure within the scope of the technical concept of the present disclosure, including a combination of individual technical features in any other suitable manner, such simple modifications and combinations thereof shall also be regarded as the content disclosed by the present disclosure, each of them falls into the protection scope of the present disclosure.

The invention claimed is:

1. A catalyst system comprising a porous material layer containing an active metal component and a molecular sieve layer,
    wherein the active metal component is a metal atom having light hydrocarbon arylation conversion activity or carbon dioxide conversion activity, wherein the active metal component is one or more selected from the group consisting of Zn, Pt, Ni, Co, Mn, Ti, Ga, Sn, Pd, Rh, Ru, Mo, W, Ir, Au, Ag, Re and Bi, wherein the light hydrocarbon is C2-C4 hydrocarbon, and wherein the carbon dioxide conversion is catalytic conversion of carbon dioxide to carbon monoxide,
    wherein during light hydrocarbon arylation or carbon dioxide conversion in a hydrogen-containing atmosphere under a temperature of 500-700° C., a pressure of 0.01-2 MPa, and a hydrogen flow rate of 10-200 sccm, the active metal component migrates into the molecular sieve layer and is captured by the molecular sieve in the molecular sieve layer.

2. The catalyst system of claim 1, wherein a weight ratio of the porous material layer containing an active metal component to the molecular sieve layer is 1:0.1-10.

3. The catalyst system of claim 1, wherein a weight ratio of the active metal component to the porous material is 1:5-1,000.

4. The catalyst system of claim 1, wherein the porous material containing an active metal component is prepared through the following method: impregnating the porous material powder with a solution containing a precursor of the active metal component, then calcining the impregnated material in an oxygen-containing atmosphere at 400-700° C. for 2-6 hours.

5. The catalyst system of claim 1, wherein the porous material is a metal oxide.

6. The catalyst system of claim 5, wherein the porous material is one or more selected from the group consisting of alumina, silicon oxide, zirconium oxide, titanium oxide, cerium oxide, tungsten oxide and molybdenum oxide.

7. The catalyst system of claim 1, wherein the molecular sieve is a zeolitic molecular sieve having a microporous structure.

8. The catalyst system of claim 7, wherein the molecular sieve is a zeolitic molecular sieve having a MFI or MEL structure.

9. The catalyst system of claim 1, wherein the porous material layer and the molecular sieve layer are in direct contact or alternately arranged.

10. The catalyst system of claim 9, wherein an inert material layer is filled between the porous material layer and the molecular sieve layer when the porous material layer and the molecular sieve layer are alternately arranged.

11. The catalyst system of claim 9, wherein a ratio of the distance separating the porous material layer and the molecular sieve layer relative to a thickness of the molecular sieve layers is 0-10:1.

12. A light hydrocarbon aromatization method, the method comprises sequentially contacting the light hydrocarbons with the porous material layer and the molecular sieve layer of the catalyst system of claim 1 under light hydrocarbon aromatization conditions.

13. The method of claim 12, wherein the light hydrocarbons are one or more selected from the group consisting of methane, ethane, propane, butane and pentane; the light hydrocarbon aromatization conditions comprise a pressure of 0.01-2 MPa on a gauge pressure basis; a temperature of 300° C.-700° C.; and a volumetric hourly space velocity of light hydrocarbons being 500 $h^{-1}$-50,000 $h^{-1}$.

14. A process for producing carbon monoxide by hydrogenation and reduction of carbon dioxide, the process comprises contacting a mixed gas of carbon dioxide and hydrogen sequentially with a porous material layer and a molecular sieve layer of the catalyst system of claim 1, under carbon dioxide hydrogenation and reduction conditions.

15. A method for enhancing the catalytic activity and/or lifetime of the catalyst during a heterogeneous catalysis process, the method comprises providing and/or replenishing metal active sites in-situ in a catalyst system by means of a metal migration method, the catalyst system is the catalyst system of claim 1.

16. The method of claim 15, wherein the metal migration method comprises that the active metal component is migrated into a molecular sieve layer, and is captured by a molecular sieve in the molecular sieve layer during the reaction process, thereby providing and/or replenishing in-situ metal active sites during the reaction process.

17. The method of claim 16, wherein the metal migration method is performed in a hydrogen-containing atmosphere, and/or performed under the conditions consisting of a temperature of 500-700° C., a pressure of 0.01-2 MPa, and a hydrogen flow rate of 10-200 sccm, and/or performed under the light hydrocarbon aromatization conditions, or carbon dioxide hydrogenation and reduction conditions.

* * * * *